United States Patent [19]

Allain et al.

[11] 3,956,069
[45] May 11, 1976

[54] ENZYMATIC ASSAYS FOR GLUCOSE, CREATINE PHOSPHOKINASE OR PLASMA AMMONIA

[75] Inventors: Charles C. Allain, Los Angeles; Carl P. Henson, Alhambra, both of Calif.

[73] Assignee: Abbott Laboratories, North Chicago, Ill.

[22] Filed: Apr. 29, 1974

[21] Appl. No.: 465,039

[52] U.S. Cl. .......................... 195/103.5 R; 195/63; 195/99; 195/103.5 C
[51] Int. Cl.$^2$ ..................... G01N 31/14; C07G 7/02
[58] Field of Search ............. 195/103.5 R, 103.5 C, 195/63, 99; 23/230 B

[56] References Cited
UNITED STATES PATENTS

| | | | |
|---|---|---|---|
| 3,388,044 | 6/1968 | Babson | 195/103.5 R |
| 3,540,984 | 11/1970 | Deutsch | 195/103.5 R |
| 3,764,478 | 10/1973 | Bergmeyer et al. | 195/103.5 R X |
| 3,778,350 | 12/1973 | Bergmeyer et al. | 195/103.5 C |

OTHER PUBLICATIONS

Rosalki, S. B., An Improved Procedure for Serum Creatine Phosphokinase Determination, J. Lab. & Chem. Med., Vol. 69, No. 4, 1967, (pp. 696–705).

Novoa et al., Lactic Dehydrogenase, J. Biol. Chem., Vol. 234, No. 5, 1959, (pp. 1143–1148).

*Primary Examiner*—David M. Naff
*Attorney, Agent, or Firm*—Gildo E. Fato; Robert L. Niblack

[57] ABSTRACT

Enzymatic assays for determining glucose, creatine phosphokinase or plasma ammonia, wherein nicotinamide adenine dinucleotide is reduced or the reduced form of nicotinamide adenine dinucleotide is oxidized to nicotinamide adenine dinucleotide, are carried out in the presence of about 2 to 50 micromoles per liter of oxalic acid or oxamic acid, or salts thereof. The oxalic acid, oxamic acid and salts thereof inhibit lactic dehydrogenase which causes errors in the assays.

9 Claims, No Drawings

ENZYMATIC ASSAYS FOR GLUCOSE, CREATINE PHOSPHOKINASE OR PLASMA AMMONIA

BACKGROUND OF THE INVENTION

In the optical method for the determination of glucose, hexokinase (HK) catalyzes the phosphorylation of glucose by adenosine triphosphate (ATP) as follows:

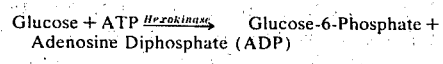

Glucose + ATP $\xrightarrow{Hexokinase}$ Glucose-6-Phosphate + Adenosine Diphosphate (ADP)

Glucose-6-phosphate (G-6-P) is oxidized in the presence of nicotinamide adenine dinucleotide (NAD) by glucose-6-phosphate dehydrogenase (G-6-PDH):

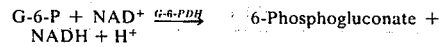

G-6-P + NAD$^+$ $\xrightarrow{G\text{-}6\text{-}PDH}$ 6-Phosphogluconate + NADH + H$^+$ The reduction of NAD to NADH (reduced form of NAD) at 340 nanometers (nm) is a quantitative measure of the amount of glucose present.

In the creatine phosphokinase (CPK) assay method of Rosalki, s. b., *Journal of Laboratory and Clinical Medicine*, 69; 696 1967), CPK catalyzes the reversible formation of adenosine triphosphate (ATP) and creatine from adenosine diphosphate (ADP) and creatine phosphate (CPO$_4$) according to the equation:

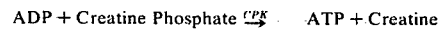

ADP + Creatine Phosphate $\underset{}{\overset{CPK}{\rightleftarrows}}$ ATP + Creatine The ATP formed in the CPK mediated reaction is used to phosphorylate glucose in the presence of hexokinase (HK) producing glucose-6-phosphate. As glucose-6-phosphate is formed, ADP is generated keeping its concentration at a constant level.

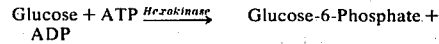

Glucose + ATP $\xrightarrow{Hexokinase}$ Glucose-6-Phosphate + ADP

The glucose-6-phosphate formed by the hexokinase reaction is then oxidized by the enzyme glucose-6-phosphate dehydrogenase (G-6-PDH) with simultaneous reduction of NAD.

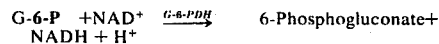

G-6-P + NAD$^+$ $\xrightarrow{G\text{-}6\text{-}PDH}$ 6-Phosphogluconate + NADH + H$^+$ The reduction of NAD to NADH is followed spectrophotometrically by observing the resulting increase in absorbance at 340 nm. For each mole of phosphate transferred by the CPK, one mole of NADH is formed. Thus the rate of absorbance change is directly proportional to the CPK activity present in the sample.

Lactic dehydrogenase (LDH) (L-Lactate:NAD oxidoreductase catalyzes the following reaction:

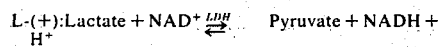

L-(+):Lactate + NAD$^+$ $\underset{H^+}{\overset{LDH}{\rightleftarrows}}$ Pyruvate + NADH +

In assaying for serum constituents other than LDH, any LDH present may cause interference due to the presence of either lactate or pyruvate in the sample, thus causing errors in the assay of glucose or CPK or in any assay system where NAD is reduced to NADH. Any NADH generated is subject to reaction with pyruvate in the presence of LDH, thus causing errors in the assay of glucose or CPK, for example.

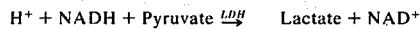

H$^+$ + NADH + Pyruvate $\xrightarrow{LDH}$ Lactate + NAD$^+$

This interference may be overcome or avoided by the use of NADP as follows:

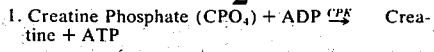

1. Creatine Phosphate (CPO$_4$) + ADP $\xrightarrow{CPK}$ Creatine + ATP

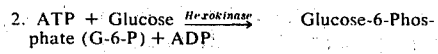

2. ATP + Glucose $\xrightarrow{Hexokinase}$ Glucose-6-Phosphate (G-6-P) + ADP

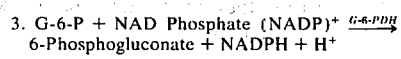

3. G-6-P + NAD Phosphate (NADP)$^+$ $\xrightarrow{G\text{-}6\text{-}PDH}$ 6-Phosphogluconate + NADPH + H$^+$ NADP and NADPH do not react with LDH present in common biological samples; however, the use of NADP in the enzymatic determination of either CPK or glucose increases the cost of the reagent and reduces the dynamic range of the method. The use of NAD in place of NADH results in reduced costs of reagent and increased dynamic range but permits undesirable reactions and the possibility of error as hereinbefore described.

SUMMARY OF THE INVENTION

It has been found that LDH forms an inactive complex with oxalic or oxamic (oxaminic)acid and their salts, thus eliminating interferences due to the presence of LDH. The concentration of oxalic or oxamic acid or salts thereof should not be in such concentration as to inhibit or interfere with the constituents being measured but should be sufficient to inhibit the reaction of LDH. Generally a concentration of from two to nine micromoles per liter is sufficient. Up to fifty micromoles can be used for high levels of pyruvate or lactate in the presence of LDH, the appropriate concentration therefore ranging from about 2 to 50 micromoles per liter of reagent solution. The method can be employed with any assay system where NAD is reduced to NADH and where the presence of pyruvate and/or LDH would be undesirable.

The method of the present invention can also be employed in assay systems wherein NADH is oxidized to NAD in order to prevent interference by pyruvate or lactate in a sample which contains LDH. In such reactions, the disappearance of NADH is a quantitative measure of the constituent which is being measured. As example is the measurement of plasma ammonia using glutamic dehydrogenase.

In the publication by Von F. Da Fonseca-Wollheim entitled "*Direkte Plasmaammoniakbestimmung Ohne Enteiweissung*" *Z. Klin. Chem. Klin. Biochem.* 11, 426–431, 1973, an assay system for plasma ammonia is described and it is pointed out that unspecific changes in extinction upon initiation of the reaction are avoided by using reduced NAD phosphate (NADPH) in place of NADH as the coenzyme. This procedure uses 0.5 ml. of plasma with 1.5 ml. of reagent. Since the sample is not deproteinized, pyruvate and LDH in the sample can react with NADH and therefore be measured as apparent ammonia. Since normal ammonia levels are quite low, less than 60 micromoles per liter, equivalent to 0.1 milligrams percent, even a small interference by pyruvate or other keto acids would be highly detrimental to the assay. It is therefore apparent that in assays employing reactions in which NADH is consumed and in which interference can occur, use of the herein described method would eliminate such interferences.

DETAILED DESCRIPTION

The present invention is exemplified by use of oxalate as the free acid or potassium salt in both the CPK or glucose assays as previously described. Oxalate is effective in preventing interference by high levels of pyruvate or lactate in the presence of LDH, thus enabling one to substitute NAD for NADP. The oxalate used may be part of the buffer system or included as a separate ingredient. The advantages of using NAD rather than NADP are decreased cost and increased dynamic range.

CPK

The effect of pyruvate at a level of 100 milligram percent in the sample tested is shown in Table I. Using NADP, there is no effect because LDH does not utilize NADP. With NAD, the presence of pyruvate causes a decrease in apparent CPK activity due to the conversion of pyruvate to lactate and subsequent oxidation of NADH. When the reaction of samples containing 100 milligram percent pyruvate is run in the presence of 2.63 millimoles per liter of oxalate (Table 2), the interference due to LDH is obviated.

TABLE 1

CPK (International Units/Liter)
Effect of Pyruvate on CPK Activity

| NADP | | NAD | |
|---|---|---|---|
| Control (No Pyruvate) | 100 mg% Pyruvate | Control (No Pyruvate No Oxalate) | 100 mg% Pyruvate (No Oxalate) |
| 9 | 10 | 11 | 14 |
| 78 | 80 | 83 | 80 |
| 9 | 9 | 13 | 9 |
| 455 | 461 | 490 | 469 |
| 65 | 65 | 70 | 64 |
| 102 | 104 | 106 | 99 |
| 717 | 726 | 845 | 833 |
| 31 | 31 | 32 | 28 |
| 19 | 20 | 25 | 22 |
| 16 | 17 | 20 | 17 |

TABLE 2

CPK (International Units/Liter)
Effect of Oxalate on CPK Activity of Samples Containing 100 mg% Pyruvate

| Control (No Pyruvate) | Test (100 mg% Pyruvate in 2.63 mmole/liter Oxalate |
|---|---|
| 10 | 10 |
| 74 | 73 |
| 11 | 11 |
| 422 | 428 |
| 57 | 58 |
| 92 | 93 |
| 726 | 740 |
| 29 | 27 |
| 22 | 21 |
| 18 | 18 |

EXAMPLE I

The following is an example of a reagent employing NAD in the presence of magnesium and activator and suitable for the enzymatic determination of creatine phosphokinase.

2 to 9 millimoles of oxalate per liter of reagent in the form of potassium oxalate is added to prevent the noted side reaction together with a suitable buffer to maintain the pH in the range of 6.1 to 7.0. Dithioerythritol in the amount of from 2 to 25 millimoles per liter of solution is satisfactory as an activator.

GLUCOSE

The effect of pyruvate on glucose determinations is shown in Table 3, giving lower values due to the presence of pyruvate and LDH causing oxidation of the NADH formed. When oxalate is included in the formulation, pyruvate shows no interference in the presence of LDH (Tables 4 and 5).

TABLE 3

Glucose (mg%)
Effect of Pyruvate on Glucose Determinations (Native Sera)

| Control (No Pyruvate) | Test (100 mg% Pyruvate) |
|---|---|
| 64 | 57 |
| 86 | 77 |
| 95 | 83 |
| 78 | 62 |
| 96 | 80 |
| 75 | 61 |
| 80 | 67 |
| 93 | 81 |
| 152 | 139 |
| 76 | 65 |

TABLE 4

Glucose (mg%)
Effect of Oxalate on Samples Containing Pyruvate (200 mg%)

| Control (No Pyruvate) (39.6 mmole/liter Oxalate) | Test (200 mg% Pyruvate in 39.6 mmole/liter Oxalate |
|---|---|
| 86 | 87 |
| 105 | 105 |
| 92 | 92 |
| 24 | 24 |
| 227 | 228 |
| 81 | 80 |
| 80 | 81 |
| 286 | 283 |
| 76 | 76 |
| 73 | 74 |
| 86 | 86 |

TABLE 5

Glucose (mg%)
Effect of Oxalate on Determination of Glucose in Presence and Absence of Pyruvate

| Control (No Oxalate No Pyruvate | 100 mg% Pyruvate No Oxalate | 100 mg% Pyruvate 9 mmole/liter Oxalate |
|---|---|---|
| 123 | 71 | 124 |
| 67 | 24 | 67 |
| 52 | 12 | 52 |

| Ingredient | Quantity Per 3 ml. Assay | Quantity Per Milliliter of Reagent |
|---|---|---|
| adenosine diphosphate (ADP) | 0.5 – 5 milligrams | 0.16 – 1.6 milligrams |
| creatine phosphate (CPO$_4$) | 10 – 30 milligrams | 3 – 10 milligrams |
| glucose | 5 – 20 milligrams | 1.6 – 6.6 milligrams |
| nicotinamide adenine dinucleotide (NAD) | 2 – 6 milligrams | 0.6 – 2 milligrams |
| hexokinase (HK) | 2 – 10 international units | 0.6 – 3.3 international units |
| glucose-6-phosphate dehydrogenase (G-6-PDH) | 5.0 – 15.0 international units | 1.6 – 5.0 international units |
| magnesium aspartate | 2 – 20 milligrams | 0.6 – 6.6 milligrams |

TABLE 5-continued

Glucose (mg%)
Effect of Oxalate on Determination of Glucose
in Presence and Absence of Pyruvate

| Control (No Oxalate No Pyruvate) | 100 mg% Pyruvate No Oxalate | 100 mg% Pyruvate 9 mmole/liter Oxalate |
|---|---|---|
| 81 | 34 | 82 |
| 50 | 9 | 49 |
| 26 | 0 | 27 |
| 76 | 30 | 75 |
| 68 | 23 | 69 |
| 82 | 31 | 82 |
| 65 | 22 | 66 |

EXAMPLE II

The following is an example of a reagent employing NAD in the presence of magnesium and suitable for the enzymatic determination of glucose.

| Ingredient | Quantity Per 3 ml. Assay | Quantity Per Milliliter of Reagent |
|---|---|---|
| adenosine triphosphate (ATP) | 0.5 – 5.0 milligrams | 0.16 – 1.6 milligrams |
| nicotinamide adenine dinucleotide (NAD) | 0.5 – 5.0 milligrams | 0.16 – 1.6 milligrams |
| hexokinase (HK) | 0.5 – 5.0 international units | 0.16 – 1.6 international units |
| glucose-6-phosphate dehydrogenase (G-6-PDH) | 0.5 – 5.0 international units | 0.16 – 1.6 international units |
| magnesium aspartate | 2 – 10 milligrams | 0.6 – 3.3 milligrams |

2 to 9 millimoles of oxalate per liter of reagent in the form of potassium oxalate is added to prevent the noted side reaction. A suitable buffer is added to maintain the pH at about 7.5.

The ingredients of the reagents of either Examples I and II may be mixed to provide a product. Accordingly, a single, dry, stable reagent for the enzymatic assay of glucose or creatine phosphokinase is provided.

The studies reported in Tables 1 through 5 were carried out at a temperature of 37° C, using a total volume of reagent and sample of 3.02 milliliters, including 0.02 milliliters of sample. A recording spectrophotometer, such as the Perkin-Elmer model 124, can be used for making the determination.

The reagents of Examples I and II can be reconstituted by adding a quantity of distilled water and gently mixing to dissolve the contents. The reagents are stable at room temperature for 6 months and in solution for at least 8 hours at room temperature or 24 hours at 4° C.

In use, the reconstituted reagent is separated into 3.0 ml. aliquot portions, to each of which is added 0.02 ml. of sample. The mixture is incubated at 37°C. for at least 10 minutes and the absorbance is recorded versus a reagent blank to determine the concentration of the ingredient being measured.

While 3.0 milliliter portions of reagent were employed in the studies reported herein, other quantities can be used as desired. The concentrations indicated in Examples I and II refer to the reagent in the form of a solution or to a dry powder mixture which, upon reconstituting in the desired amount of water or other solvent, will provide the indicated concentrations.

What is claimed is:

1. In an enzymatic assay of a sample for measurement of glucose, creatine phosphokinase, and plasma ammonia wherein nicotinamide adenine dinucleotide is reduced or the reduced form of nicotinamide adenine dinucleotide is oxidized to nicotinamide adenine dinucleotide, said reduced form or disappearance of said reduced form of nicotinamide adenine dinucleotide being a quantitative measure of the constituent in said sample which is being measured and being subject to reaction with pyruvate in the presence of lactic dehydrogenase to thereby cause errors in said assay, the improvement comprising:

conducting said assay in the presence of a compound selected from the class consisting of oxalic acid and oxamic acid or salts thereof, the concentration of said compound ranging from about 2 to 50 micromoles per liter of reagent solution and being sufficient to inhibit the reaction of lactic dehydrogenase while at the same time not interfering with the constituents being measured, whereby said compound forms an inactive complex with lactic dehydrogenase to thereby eliminate interference and minimize any errors in said assay.

2. In an enzymatic assay method for the determination of glucose in a sample, said method comprising the steps of:

phosphorylation of glucose in said sample by adenosine triphosphate in the presence of hexokinase to form glucose-6-phosphate;

oxidation of the glucose-6-phosphate in the presence of nicotinamide adenine dinucleotide by glucose-6-phosphate dehydrogenase to produce the reduced form of nicotinamide adenine dinucleotide;

measuring the amount of the reduced form of nicotinamide adenine dinucleotide to determine the glucose present in the sample;

the improvement comprising conducting said assay in the presence of a compound selected from the class consisting of oxalic acid and oxamic acid or salts thereof, the concentration of said compound being sufficient to inhibit the reaction of any lactic dehydrogenase present in the sample, and ranging from about 2 to 50 micromoles per liter of reagent solution.

3. The method of claim 2 wherein the concentration of said compound is from 2 to 9 micromoles per liter of reagent solution.

4. In an enzymatic assay method for the determination of creatine phosphokinase in a sample, said method comprising:

reacting adenosine diphosphate and creatine phosphate in the presence of creatine phosphokinase to produce adenosine triphosphate and creatine;

phosphorylating glucose with the adenosine triphosphate formed in the presence of hexokinase to produce glucose-6-phosphate;

oxidizing the glucose-6-phosphate with glucose-6-phosphate dehydrogenase in the presence of nicotinamide adenine dinucleotide to produce the reduced form of nicotinamide adenine dinucleotide;

measuring the amount of reduced nicotinamide adenine dinucleotide which is formed to determine the creatine phosphokinase activity present in the sample;

the improvement comprising conductive said assay in the presence of a compound selected from the group consisting of oxalic acid and oxamic acid or salts thereof, the concentration of said compound being sufficient to inhibit the reaction of any lactic dehydrogenase present in the sample, and ranging from about 2 to 50 micromoles per liter of reagent solution.

5. The method of claim 4 wherein the concentration of said compound is from 2 to 9 micromoles per liter of reagent solution.

6. A single reagent for conducting an enzymatic assay for the glucose content of a sample comprising a water soluble, solid, substantially anhydrous, storage stable mixture of:

adenosine triphosphate in a concentration of from 0.16 to 1.6 milligrams per milliliter of reagent;

nicotinamide adenine dinucleotide in a concentration of 0.16 to 1.6 milligrams per milliliter of reagent;

hexokinase in a concentration of from 0.16 to 1.6 international units per milliliter of reagent;

glucose-6-phosphate dehydrogenase in a concentration of from 0.16 to 1.6 international units per milliliter of reagent;

a magnesium salt in a concentration of from 0.6 to 3.3 milligrams per milliliter of reagent; and from 2 to 50 micromoles per liter of reagent solution of a compound selected from the class consisting of oxalic acid and oxamic acid or salts thereof.

7. The reagent of claim 6 wherein the concentration of said compound is from 2 to 9 micromoles per liter of reagent solution.

8. A single reagent for conducting an enzymatic assay for the creatine phosphokinase activity of a sample comprising a water soluble, solid, substantially anhydrous, storage stable mixture of:

adenosine diphosphate in a concentration of from 0.16 to 1.6 milligrams per milliliter of reagent;

creatine phosphate in a concentration of from 3 to 10 milligrams per milliliter of reagent;

glucose in a concentration of from 1.6 to 6.6 milligrams per milliliter of reagent;

nicotinamide adenine dinucloetide in a concentration of from 0.6 to 2 milligrams per milliliter of reagent;

hexokinase in a concentration of from 0.6 to 3.3 international units per milliliter of reagent;

glucose-6-phosphate dehydrogenase in a concentration of from 1.6 to 5.0 international units per milliliter of reagent;

a magnesium salt in a concentration of from 0.6 to 6.6 milligrams per milliliter of reagent; and from 2 to 50 micromoles per liter of reagent solution of a compound selected from the class consisting of oxalic acid and oxamic acid or salts thereof.

9. The reagent of claim 8 wherein the concentration of said compound is from 2 to 9 micromoles per liter of reagent solution.

* * * * *

UNITED STATES PATENT AND TRADEMARK OFFICE
CERTIFICATE OF CORRECTION

PATENT NO. : 3,956,069
DATED : May 11, 1976
INVENTOR(S) : Charles C. Allain and Carl P. Henson It is certified that error appears in the above-identified patent and that said Letters Patent are hereby corrected as shown below:

In the Abstract, the unit "micromoles" should read -- millimoles --.

Column 2, lines 28 and 29, "micromoles" should read -- millimoles --;

Column 6, lines 12, 51, and 54, "micromoles" should read -- millimoles ''; Column 7, lines 11 and 14, "micromoles" should read -- millimoles --; and Column 8, lines 1, 5, 27, and 31, "micromoles" should read -- millimoles --.

Signed and Sealed this

First Day of November 1977

[SEAL]

Attest:

RUTH C. MASON
Attesting Officer

LUTRELLE F. PARKER
Acting Commissioner of Patents and Trademarks